United States Patent
Zhou et al.

(10) Patent No.: US 9,220,169 B2
(45) Date of Patent: Dec. 22, 2015

(54) BIOCOMPATIBLE ELECTROPLATED INTERCONNECTION ELECTRONICS PACKAGE SUITABLE FOR IMPLANTATION

(75) Inventors: Dao Min Zhou, Saugus, CA (US); James Singleton Little, Saugus, CA (US); Robert J. Greenberg, Los Angeles, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 313 days.

(21) Appl. No.: 11/821,327

(22) Filed: Jun. 21, 2007

(65) Prior Publication Data

US 2008/0319493 A1    Dec. 25, 2008

(51) Int. Cl.
| | | |
|---|---|---|
| *A61N 1/36* | (2006.01) | |
| *H05K 3/36* | (2006.01) | |
| *A61N 1/02* | (2006.01) | |
| *C25D 3/62* | (2006.01) | |
| *C25D 5/02* | (2006.01) | |
| *C25D 5/18* | (2006.01) | |
| *C25D 5/56* | (2006.01) | |
| *H05K 3/32* | (2006.01) | |
| *C25D 3/56* | (2006.01) | |

(52) U.S. Cl.
CPC *H05K 3/361* (2013.01); *A61N 1/02* (2013.01); *A61N 1/36046* (2013.01); *C25D 3/62* (2013.01); *C25D 5/02* (2013.01); *C25D 5/18* (2013.01); *C25D 5/56* (2013.01); *H05K 3/32* (2013.01); *C25D 3/567* (2013.01); *H05K 2203/0723* (2013.01)

(58) Field of Classification Search
CPC ... A61N 1/0543; A61N 1/36046; A61N 1/02; C25D 5/18; H05K 3/32
USPC .................................................. 607/1, 36–38
See application file for complete search history.

(56) References Cited

U.S. PATENT DOCUMENTS

| | | | | |
|---|---|---|---|---|
| 3,284,174 | A | * | 11/1966 | Zimmer ........................ 428/547 |
| 3,360,348 | A | * | 12/1967 | Schreiner ..................... 428/547 |
| 3,699,970 | A | | 10/1972 | Brindley et al. |
| 4,573,481 | A | | 3/1986 | Bullara |
| 4,837,049 | A | | 6/1989 | Byers et al. |
| 5,006,286 | A | | 4/1991 | Dery et al. |
| 5,100,714 | A | * | 3/1992 | Zsamboky .................... 428/137 |

(Continued)

OTHER PUBLICATIONS

Hansjoerg Beutel, et al.; Versatile 'Microflex'-Based Interconnection Technique; SPIE Conf. on Smart Electronics and MEMS; Mar. 1998; pp. 174-182; vol. 3328; San Diego, CA.

(Continued)

*Primary Examiner* — George Evanisko
(74) *Attorney, Agent, or Firm* — Scott B. Dunbar; Gary Schnittgrund

(57) ABSTRACT

Device is a hermetically sealed electronics package bonded to an electrode or flexible circuit that is suitable for implantation such as for a retinal or cortical electrode array. The hermetically sealed electronics package is bonded to the electrode or flexible circuit by electroplating a biocompatible material, such as platinum or gold, forming a plated connection, bonding the flexible circuit to the electronics package. The resulting electronic device is biocompatible and is suitable for long-term implantation. The device comprises a substrate containing a contact, a flexible assembly containing a pad, and electroplated bonding between said contact and said pad that bonds said substrate and said flexible assembly together.

12 Claims, 10 Drawing Sheets

(56) References Cited

U.S. PATENT DOCUMENTS

| | | | |
|---|---|---|---|
| 5,109,844 A | 5/1992 | de Juan, Jr. et al. | |
| 5,215,088 A | 6/1993 | Normann et al. | |
| 5,468,936 A | 11/1995 | Deevi et al. | |
| 5,611,140 A | 3/1997 | Kulesza et al. | |
| 5,901,336 A * | 5/1999 | Dombrowski | 419/6 |
| 5,935,155 A | 8/1999 | Humayun et al. | |
| 5,988,488 A * | 11/1999 | Slattery et al. | 228/262.6 |
| 6,089,444 A * | 7/2000 | Slattery et al. | 228/194 |
| 6,139,975 A * | 10/2000 | Mawatari et al. | 428/600 |
| 6,361,716 B1 | 3/2002 | Kleyer et al. | |
| 6,400,989 B1 | 6/2002 | Eckmiller | |
| 6,458,157 B1 | 10/2002 | Suaning | |
| 7,211,103 B2 | 5/2007 | Greenberg et al. | |
| 7,498,001 B2 * | 3/2009 | Tonkovich et al. | 422/615 |
| 2003/0233134 A1 * | 12/2003 | Greenberg et al. | 607/36 |

OTHER PUBLICATIONS

L. Del Castillo, et al.; Flip Chip Packaging of a MEMS Neuro-Prosthetic System; IMAPS Int. Conf. & Exh. on Advanced Packaging and Systems; Mar. 2002; pp. 158-163; Reno, NV.

Marcel Pourbaix, Atlas of Electrochemical Equilibria in Aqueous Solutions; National Association of Corrosion Engineers; 1974; 9 pages; Houston, TX.

* cited by examiner

BIOCOMPATIBLE ELECTROPLATED INTERCONNECTION ELECTRONICS PACKAGE SUITABLE FOR IMPLANTATION

FEDERALLY SPONSORED RESEARCH

This invention was made with government support under grant No. R24EY12893-01, awarded by the National Institutes of Health. The government has certain rights in the invention.

FIELD OF THE INVENTION

This invention relates to an electrode array or flexible circuit, electronics package and a method of bonding a flexible circuit or electrode array to an integrated circuit or electronics package.

BACKGROUND OF THE INVENTION

Arrays of electrodes for neural stimulation are commonly used for a variety of purposes. Some examples include U.S. Pat. No. 3,699,970 to Brindley, which describes an array of cortical electrodes for visual stimulation. Each electrode is attached to a separate inductive coil for signal and power. U.S. Pat. No. 4,573,481 to Bullara describes a helical electrode to be wrapped around an individual nerve fiber. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. U.S. Pat. No. 5,109,844 to de Juan describes a flat electrode array placed against the retina for visual stimulation. U.S. Pat. No. 5,935,155 to Humayun describes a retinal prosthesis for use with a flat retinal array.

Packaging of a biomedical device intended for implantation in the eye, and more specifically for physical contact with the retina, presents a unique interconnection challenge. Biocompatible bonding method and electronics package suitable for implantation are described in U.S. Pat. Nos. 7,211,103 and 7,142,909 as well as in U.S. Patent applications Nos. 2007/0021787 and 2007/0005112. The consistency of the retina is comparable to that of wet tissue paper and the biological media inside the eye is a corrosive saline liquid environment.

Thus, the device to be placed against the retina, in addition to being comprised of biocompatible, electrochemically stable materials, must appropriately conform to the curvature of the eye, being sufficiently flexible and gentle in contact with the retina to avoid tissue damage, as discussed in Andreas Schneider, Thomas Stieglitz, Werner Haberer, Hansjörg Beutel, and J.-Uwe Meyer, "Flexible Interconnects for Biomedical Microsystems Assembly, IMAPS Conference, Jan. 31, 2001. It is also desirable that this device, an electrode array, provides a maximum density of stimulation electrodes. A commonly accepted design for an electrode array is a very thin, flexible conductor cable. It is possible to fabricate a suitable electrode array using discrete wires, but with this approach, a high number of stimulation electrodes cannot be achieved without sacrificing cable flexibility (to a maximum of about 16 electrodes).

A lithographically fabricated thin film flex circuit electrode array overcomes such limitations. A thin film flex circuit electrode array can be made as thin as 10 um (0.0004 inches) while accommodating about 60 electrodes in a single circuit routing layer. The flex circuit electrode array is essentially a passive conductor ribbon that is an array of electrode pads, on one end, that contact the retina and on the other end an array of bond pads that must individually mate electrically and mechanically to the electrical contacts of a hermetically sealed electronics package. These contacts may emerge on the outside of the hermetic package as an array of protruding pins or as vias flush to a package surface. A suitable interconnection method must not only serve as the interface between the two components, but must also provide electrical insulation between neighboring pathways and mechanical fastening between the two components.

Many methods exist in the electronics industry for attaching an integrated circuit to a flexible circuit. Commonly used methods include wire-bonding, anisotropic-conductive films, and "flip-chip" bumping. However, none of these methods results in a biocompatible connection. Common materials used in these connections are tin-lead solder, indium and gold. Each of these materials has limitations on its use as an implant. Lead is a known neurotoxin. Indium corrodes when placed in a saline environment.

In many implantable devices, the package contacts are feedthrough pins to which discrete wires are welded and subsequently encapsulated with polymer materials. Such is the case in heart pacemaker and cochlear implant devices. Flexible circuits are not commonly used, if at all, as external components of proven implant designs. The inventor is unaware of prior art describing the welding of contacts to flex circuits.

Attachment by gold ball bumping has been demonstrated by the Fraunhofer group (see Hansjoerg Beutel, Thomas Stieglitz, Joerg Uwe Meyer, "Versatile 'Microflex'-Based Interconnection Technique," Proc. SPIE Conf on Smart Electronics and MEMS, San Diego, Cal., March 1998, vol 3328, pp 174-82) to rivet a flex circuit onto an integrated circuit. A robust bond can be achieved in this way. However, encapsulation proves difficult to effectively implement with this method. Because the gap between the chip and the flex circuit is not uniform, under fill with epoxy is not practical. Thus, electrical insulation cannot be achieved with conventional under fill technology.

Widespread use of flexible circuits can be found in high volume consumer electronics and automotive applications, such as stereos. These applications are not constrained by a biological environment. Component assembly onto flex circuits is commonly achieved by solder attachment. These flex circuits are also much more robust and bulkier than a typical implantable device. The standard flex circuit on the market is no less than 0.002 inches in total thickness. The trace metallization is etched copper foil, rather than thin film metal. Chip-scale package (CSP) assembly onto these flex circuits is done in ball-grid array (BGA) format, which uses solder balls attached to input-output contacts on the package base as the interconnect structures. The CSP is aligned to a corresponding metal pad array on the flex circuit and subjected to a solder reflow to create the interconnection. A metallurgical interconnect is achieved by solder wetting. The CSP assembly is then underfilled with an epoxy material to insulate the solder bumps and to provide a pre-load force from the shrinkage of the epoxy.

Direct chip attach methods are referred to as chip-on-flex (COF) and chip-on-board (COB). There have been some assemblies that utilize gold wirebonding to interconnect bare, integrated circuits to flexible circuits. The flipchip process is becoming a reliable interconnect method. Flipchip technology originates from IBM's Controlled Collapse Chip Connection (C4) process, which evolved to solder reflow technique. Flipchip enables minimization of the package footprint, saving valuable space on the circuit, since it does not require a fan out of wirebonds. While there are a variety of flipchip configurations available, solder ball attach is the most common method of forming interconnects. A less developed approach to flipchip bonding is the use of conductive adhesive, such as epoxy or polyimide, bumps to replace solder balls. These bumps are typically silver-filled epoxy or polyimide, although electrically conductive particulate of select biocompatible metal, such as platinum, iridium, titanium, platinum alloys, iridium alloys, or titanium alloys in dust, flake, or powder form, may alternatively be used. This method does not achieve a metallurgical bond, but relies on adhesion. Polymer bump flip chip also requires underfill encapsulation. Conceivably, polymer bump attachment could be used on a chip scale package as well. COB flipchip attach can also be achieved by using gold stud bumps, as an alternative to solder balls. The gold bumps of the chip are bonded to gold contacts on the hard substrate by heat and pressure. A recent development in chip-to-package attachment was introduced by Intel Corporation as Bumpless Build Up Layer (BBUL) technology. In this approach, the package is grown (built up) around the die rather than assembling the die into a pre-made package. BBUL presents numerous advantages in reliability and performance over flipchip.

Known technologies for achieving a bond between a flexible circuit and an electronics package suffer from biocompatibility issues. Novel applications of a biomedical implant that utilize a flexible circuit attached to a rigid electronics package require excellent biocompatibility coupled with long term mechanical attachment stability, to assure long lived reliable electrical interconnection.

Known deposition techniques for a bond, such as an electrically conductive metal bond or "rivet" are limited to thin layers. Plating is one such known method that does not result in an acceptable bond. It is not known how to plate shiny platinum in layers greater than approximately 1 to 5 microns because the dense platinum layer peels off, probably due to internal stresses. Black platinum lacks the strength to be a good mechanical attachment, and also lack good electrical conductivity.

Known techniques for bonding an electronic package to a flex circuit do not result in a hermetic package that is suitable for implantation in living tissue. Therefore, it is desired to have a method of attaching a substrate to a flexible circuit that ensures that the bonded electronic package and flex circuit will function for long-term implant applications in living tissue.

SUMMARY OF THE INVENTION

An implantable electronic device comprising a hermetic electronics control unit, which is typically mounted on a substrate which is bonded to a flexible circuit by an electroplated platinum or gold interconnection bonding. The resulting electronics assembly is biocompatible and long-lived when implanted in living tissue, such as in an eye or ear.

The novel features of the invention are set forth with particularity in the appended claims. The invention will be best understood from the following description when read in conjunction with the accompanying drawings.

OBJECTS OF THE INVENTION

It is an object of the invention to provide a hermetic, biocompatible electronics package that is attached to a flexible circuit.

It is an object of the invention to attach a hermetically sealed electronics package to a flexible circuit for implantation in living tissue.

It is an object of the invention to attach a hermetically sealed electronics package to a flexible circuit for implantation in living tissue to transmit electrical signals to living tissue, such as the retina.

It is an object of the invention to provide a hermetic, biocompatible electronics package that is attached directly to a substrate.

It is an object of the invention to provide a method of bonding a flexible circuit to a substrate with an electroplated interconnection bonding.

It is an object of the invention to provide a method of plating platinum or gold as an interconnection bonding.

Other objects, advantages and novel features of the present invention will become apparent from the following detailed description of the invention when considered in conjunction with the accompanying drawing.

DETAILED DESCRIPTION OF THE PREFERRED EMBODIMENTS

The present invention provides a flexible circuit electronics package and a method of bonding a flexible circuit to a hermetic integrated circuit which is useful for a number of applications, including implantation in living tissue as a neural interface, such as a retinal electrode array or an electrical sensor. The device comprises a substrate containing at least one routing (contact), a flexible assembly containing at least one pad, and electroplated bonding between said routing and said pad that bonds said substrate and said flexible assembly together.

Figure 1:
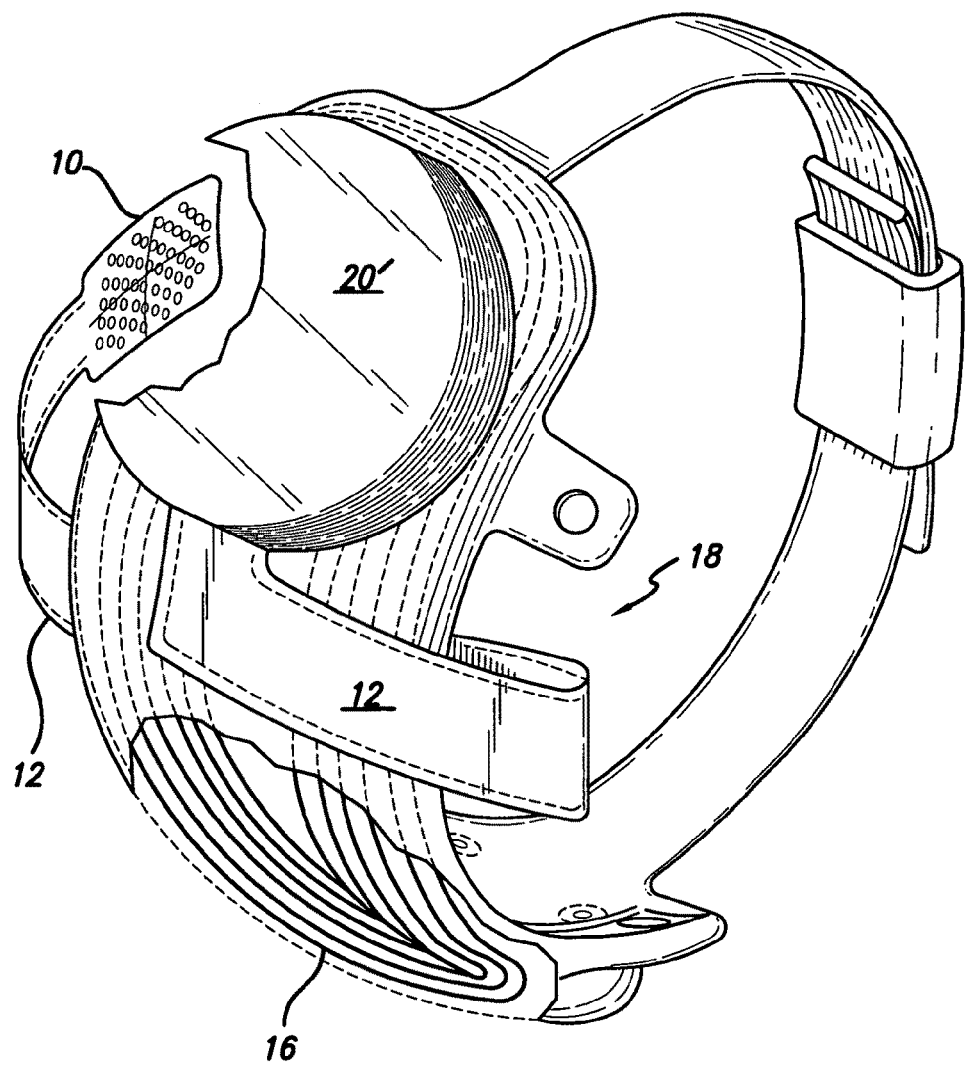
FIG. 1 illustrates a perspective cutaway view of an eye containing a flexible circuit electrode array.

The tissue paper thin flexible circuit 18, FIG. 1, transmits electrical signals to the eye by means of electrodes, that are located in a stimulating electrode array 10, that are in contact with the retina. It is obvious that in addition to a stimulating electrode array or sensing electrode, the electrodes may be contacts connecting to remote electrodes. FIG. 1 illustrates the electronics control unit 20 connected to a flexible circuit cable 12. The flexible circuit cable 12 connects the electronics control unit 20 to the stimulating electrode array 10. The electronics control unit 20 is hermetically sealed. The electronics control unit 20 may be a hermetic ceramic case with electronics inside, or it may be a hermetically sealed integrated circuit sealed by a hermetic coating such as ultra-nano crystalline diamond or deposited ceramic, or any other environmentally sealed electronics package. The stimulating electrode array 10 is implanted on the retina.

The flexible circuit ribbon 12 preferably passes through the sclera of the eye. Another embodiment of the invention is the flexible circuit ribbon 12 replaced by alternative means of electrical interconnection, such as fine wires or thin cable. A coil 16, which detects electronic signals such as of images or to charge the electronics control unit 20 power supply, located outside the eye, near the lens, is connected to the electronics control unit 20.

Figure 2:
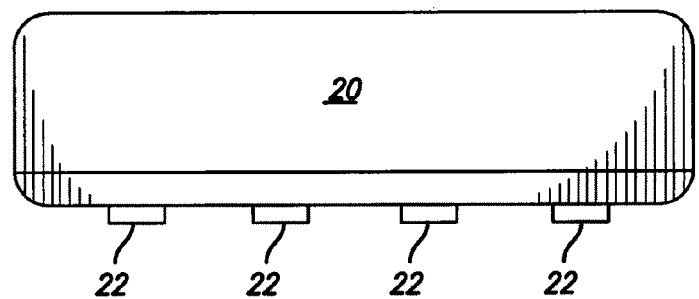
FIG. 2 is a side view of an electronics package.

FIG. 2 illustrates a side view of the hermetic electronics control unit 20 and the input/output contacts 22 that are located on the bottom of the unit 20. The input/output contacts 22 are bonded in the completed assembly to the flexible circuit 18. Thick film pad 23 is formed by known thick film technology, such as silk screening or plating.

Figure 3:
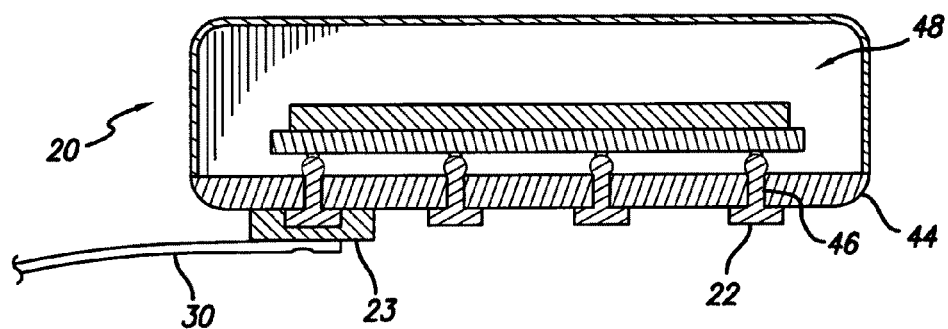
FIG. 3 illustrates a cutaway side view of an electronics package.

FIG. 3 illustrates a cutaway side view of the hermetic electronics control unit 20. The pad 23 facilitates attachment of wire 30, and is preferably comprised of a biocompatible material such as platinum, iridium, or alloys thereof, and is preferably comprised of platinum paste. Wire 30 is preferably bonded to pad 23 by welding. The microelectronics assembly 48 is mounted on the hybrid substrate 44. Vias 46 pass through the substrate 44 to input/output contacts 22. Electrical signals arrive by wire 30 and exit the electronics control unit 20 by input/output contacts 22.

Figure 4:
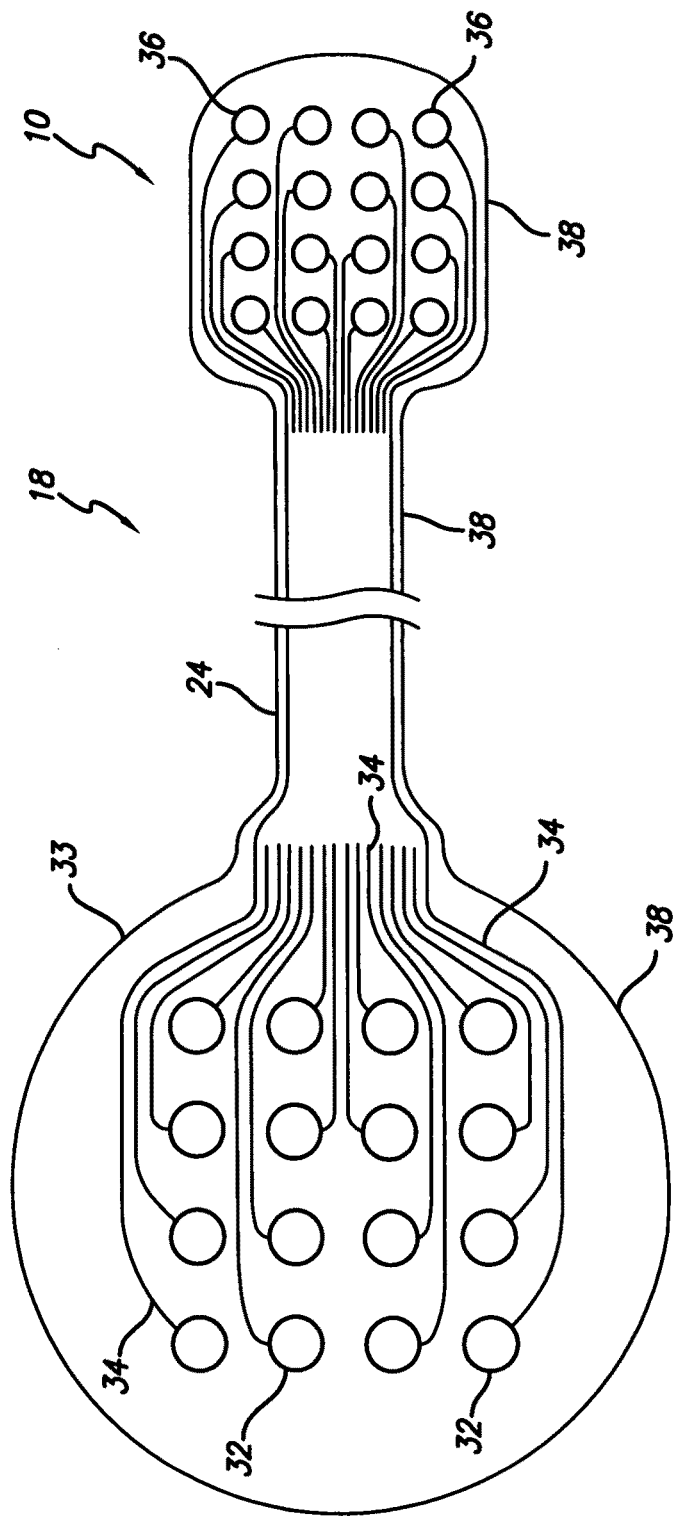
FIG. 4 is a top view of a flex circuit without the electronics package.

A top view of the flexible circuit 18 is illustrated in FIG. 4. Electrical signals from the electronics control unit 20 (see FIG. 3) pass into bond pads 32, which are mounted in bond pad end 33. Flexible electrically insulating substrate 38 is preferably comprised of polyimide. The signals pass from the bond pads 32 along traces 34, which pass along flexible circuit ribbon 12 to the stimulating electrode array 10. The array 10 contains the electrodes 36, which are implanted to make electrical contact with the retina of the eye, illustrated in FIG. 1. An alternative bed of nails embodiment for the electrodes 36 is disclosed by Byers, et al. in U.S. Pat. No. 4,837,049.

Figure 5:
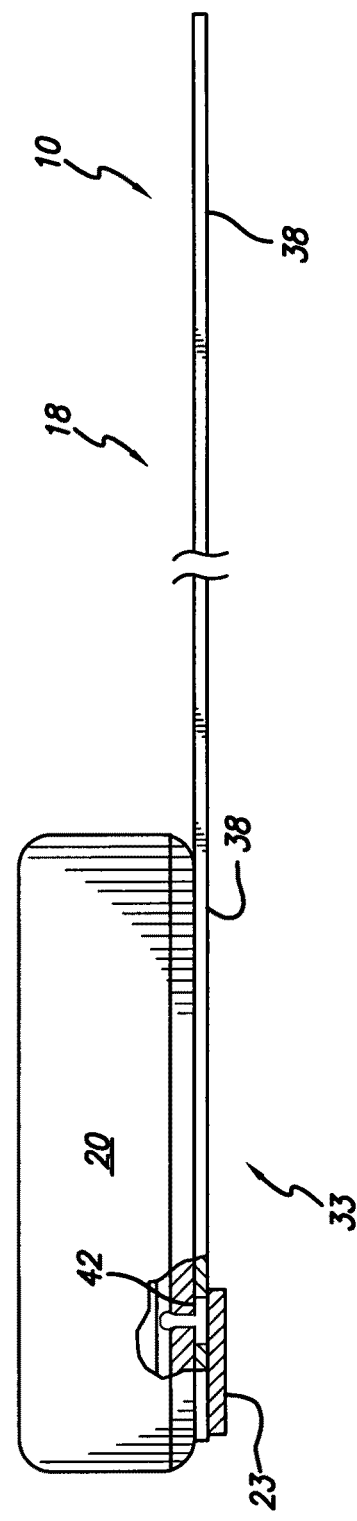
FIG. 5 presents a side view of a flex circuit with the electronics package.

In FIG. 5, the hermetic electronics control unit 20 is illustrated mounted to flexible circuit 18. In order to assure electrical continuity between the electronics control unit 20 and the flexible circuit 18, the electrical control unit 20 must be intimately bonded to the flexible circuit 18 on the bond pad end 33. A cutaway of the electronics control unit 20 (FIG. 5) illustrates a bonded connection 42. The flexible electrically insulating substrate 38 is very thin and flexible and is able to conform to the curvature of the retina, when implanted thereon.

Figure 8A:
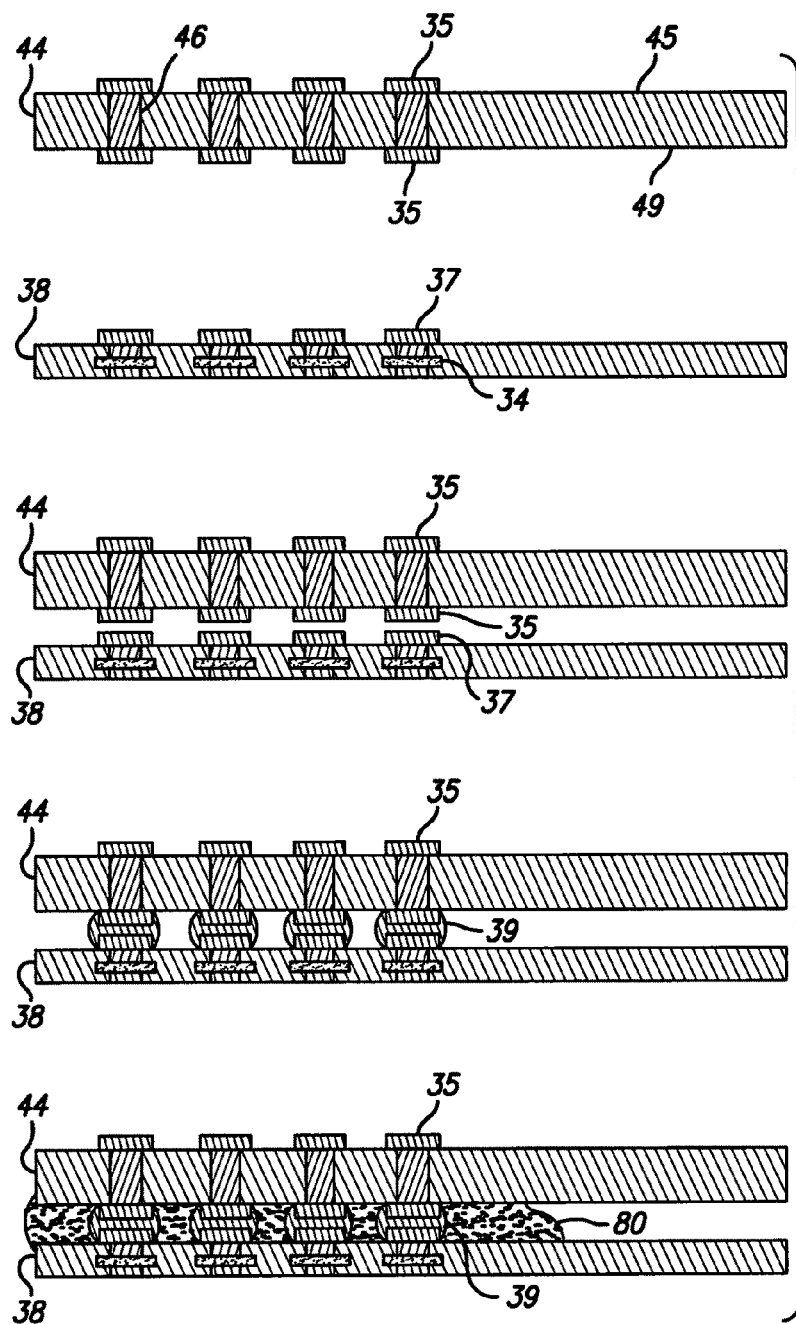
FIG. 8a is a three-electrode electroplating cell schema.

Methods of bonding the flexible insulating substrate 18 to the hermetic electronics control unit 20 are discussed next.
Interconnection Bonding by Electroplating Platinum or Gold
A preferred embodiment of the invention, illustrated in FIG. 8a shows the method of bonding the hybrid substrate 44 to the flexible circuit 38 using electroplated metal interconnection bonding 37. The metal of choices contains select biocompatible metal, such as platinum, gold, iridium, titanium, platinum alloys, gold alloys, iridium alloys, or titanium alloys.

Step a shows the hybrid substrate 44, which is preferably a ceramic, such as alumina or silicon, having a total thickness of 0.010-0.015 inches, preferably about 0.012 inches, with patterned vias 46 therethrough. The vias 46 are preferably comprised of frit containing platinum.

A routing or contact 35 is patterned on one side of the hybrid substrate 44 by known techniques, such as photolithography or masked deposition. It is equally possible to form routing 35 on both sides of the substrate 44. The hybrid substrate 44 has an inside surface 45 and an outside surface 49. The routing 35 will carry electrical signals from the integrated circuit, that is to be added, to the vias 46, and ultimately will stimulate the retina (not illustrated). The routing 35 is patterned by know processes, such as by masking during deposition or by post-deposition photolithography. The routing 35 is comprised of a biocompatible, electrically conductive, patternable material, such as platinum or gold.

Traces 34 on the outside surface 49 of the hybrid substrate 44 are deposited by a known process, such as physical vapor deposition or ion-beam assisted deposition. They may be patterned by a known process, such as by masking during deposition or by post-deposition photolithography. The traces 34 are comprised of an electrically conductive, biocompatible material, such as platinum, gold, platinum alloys, such as platinum-iridium, or titanium-platinum. The traces 34 conduct electrical signals along the flexible circuit 18 and to the stimulating electrode array 10, which were previously discussed and are illustrated in FIG. 4.

Step b illustrates formation of the flexible electrically insulating substrate 38 by known techniques, preferably liquid precursor spinning. The flexible electrically insulating substrate 38 is preferably comprised of polyimide or silicone. The flexible electrically insulating substrate electrically insulates the traces 34. It is also biocompatible when implanted in living tissue. The coating is 4 pm-6 pm, preferably about 5 pm thick. The liquid precursor is spun coated over the traces 34 and the entire outside surface 49 of the hybrid substrate 44, thereby forming the flexible electrically insulating substrate 38. The spun coating is cured by known techniques.

The contact pads 37 on the flexible substrate surface 38 are deposited by a known process, such as physical vapor deposition or ion-beam assisted deposition. They may be patterned by a known process, such as by masking during deposition or by post-deposition photolithography. The pads 37 are comprised of an electrically conductive, biocompatible material, such as platinum, gold, platinum alloys, such as platinum-iridium, or titanium-platinum.

Step c illustrates the flexible assembly 38 is placed closely next to the hybrid substrate 44 in preparation for bonding by electroplating. The pads 37 on the flexible substrate 38 are aligned with the trace contacts 35 on the hybrid substrate 44.

Step d illustrates the bonding 39 which are formed between pads 37 and contacts 35 by electroplating of a biocompatible, electrically conductive material, such as platinum, gold, conducting polymers or platinum alloys, such as platinum-iridium.

Step e illustrates the bond area is then underfilled with an adhesive 80, preferably epoxy. The hybrid substrate 44 preferably contains vias 46 that pass through the thickness of the hybrid substrate 44, see FIG. 8, step (a). Vias 46 are not required to enable this invention. It is preferred that the hybrid substrate 44 be rigid, although alternatively it can a non-rigid substrate.

A flexible electrically insulating substrate 38 is preferably comprised of two layers of an electrically insulating material, such as a polymer. Known preferred polymer materials are polyimide, silicone or Parylene. Parylene refers to polyparaxylylene, a known polymer that has excellent implant characteristics. For example, Parylene, manufactured by Specialty Coating Systems (SCS), a division of Cookson Electronic Equipment Group, located in Indianapolis, Ind., is a preferred material. Parylene is available in various forms, such as Parylene C, Parylene D, and Parylene N, each having different properties. The preferred form is Parylene C.

Referring to FIGS. 6, 7, 8a and 8b, a method to produce plated platinum or gold according to the present invention is described comprising connecting a common electrode 402, the anode, and a bonding assembly 70, the cathode, to a voltage or current source, such as a potentiostat 406 with a wave form generator 430 and monitor 428, preferably an oscilloscope. The common electrode 402, bonding assembly 70, a reference electrode 410, for use as a reference in controlling the power source, which is comprised of a voltage or current source 406 and a waveform generator 430, and an electroplating solution are placed in a electroplating cell 400 having a means for mixing 414 the electroplating solution. Power may be supplied to the electrodes with constant voltage, constant current, pulsed voltage, scanned voltage or pulsed current to drive the electroplating process. Depending on electrical connection methods, ether polymer substrate 38 or hybrid substrate 44 can be served as the cathode during electroplating. Alternatively, the polymer substrate 38 or hybrid substrate 44 can also be alternated as the cathode or both served as the cathode during electroplating.

Figure 6:
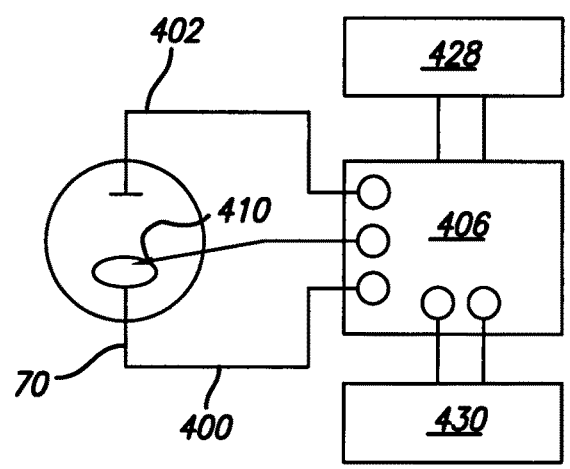
FIG. 6 is a series of illustrations of a flexible circuit being connected to a hybrid substrate using electroplated interconnection bonding.
Figure 7:
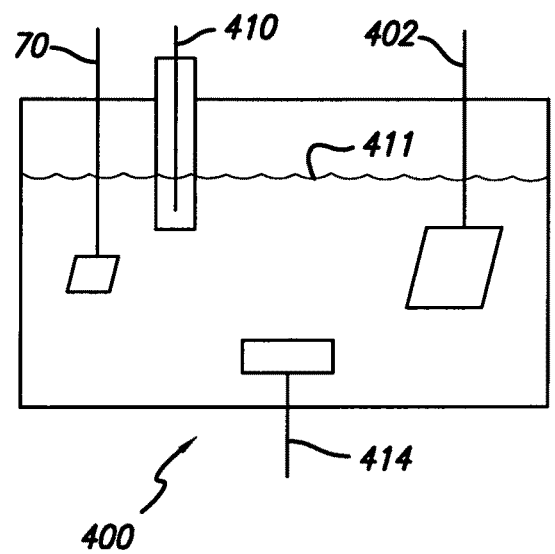
FIG. 7 is an electroplating equipment schema.

Referring to FIGS. 6 and 7, the electroplating cell 400, is preferably a 50 ml to 150 ml four neck glass flask or beaker, the common electrode 402, or anode, is preferably a large surface area platinum wire or platinum sheet, the reference electrode 410 is preferably a Ag/AgCl electrode (silver, silver chloride electrode), the bonding assembly 70, or cathode, can be any suitable material depending on the application and can be readily chosen by one skilled in the art. Preferable examples of the bonded assembly 70 include, but are not limited to, platinum, iridium, rhodium, gold, tantalum, titanium or niobium, preferably platinum.

The means for mixing 414 is preferably a magnetic stirrer (FIG. 7). The plating solution is preferably 20 to 200 millimoles gold sulphite in 50 to 500 millimoles of support electrolyte such as disodium hydrogen phosphate, alkali sulfite or sulfuric acid, but may be derived from any gold salts or other electroplating solution. The preferable plating temperature is approximately 24° to 26° C.

Figure 9:
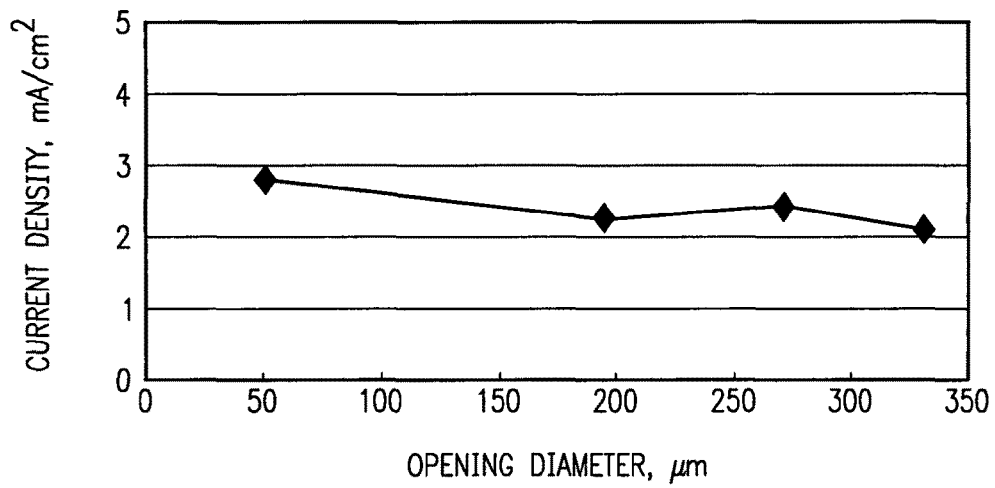
FIG. 9 is a plot showing electroplating current density variations of contact pads opening diameters during Au electroplating.
Figure 10:
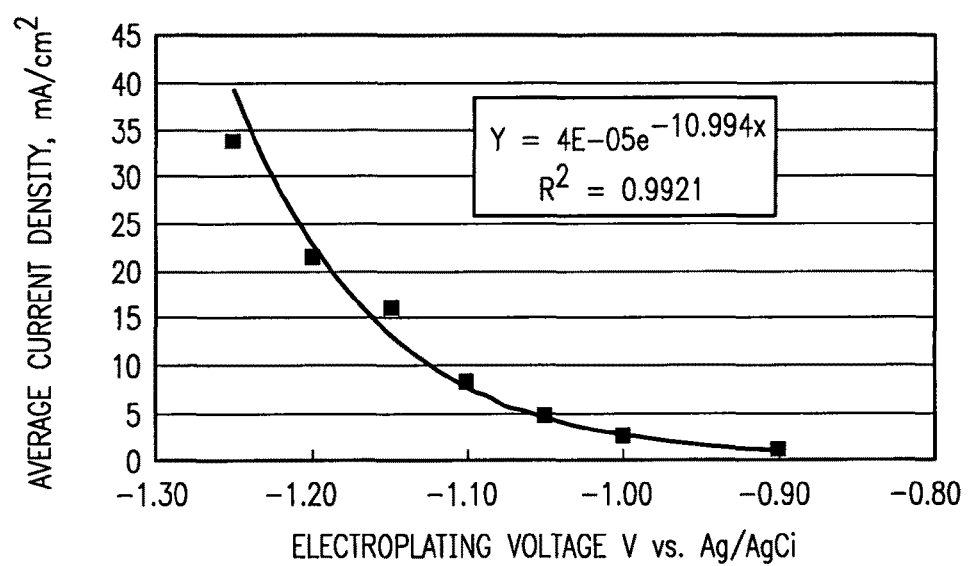
FIG. 10 is a plot of showing response current density variation with applied constant electrode voltage during Au electroplating.

The electroplating system for constant voltage control is shown in FIGS. 6 and 7. While constant voltage, constant current, pulsed voltage or pulsed current can be used to control the electroplating process, constant voltage control of the plating process is preferable for plating interconnection bonding. The preferable voltage range to produce plated gold of the present invention, which varies from about −0.7 volts to −1.25 volts. The preferable voltage range to produce plated gold is depended on the plating solution pH. At the same plating voltage, the response current density is slight higher for smaller pad openings (see FIG. 9). Generally speaking, the response current density from 0.5 to 40 mA/cm$^2$, is dependent on the electroplating voltages, see FIG. 10. Higher voltage will have a higher plating rate and a rougher surface. Applying power in this range with the above solution yields a plating rate in the range of about 0.01 µm per minute to 0.5 µm per minute, preferably 0.02 µm per minute to 0.3 µm per minute, which is the preferred range for plating rate of plated gold of the present invention. The average current density may be determined by the equation $y=4E^{-5} e^{-11x}$ ($R^2=0.992$) where y is the average current density in mA/cm$^2$ and x is the cathodic (negative) voltage in volts. Constant voltage control also allows an array of interconnection bonding to be plated simultaneously achieving uniform bonding properties.

Since low plating rate will give a dense gold layer and provide good adhesion to the seed layer, a step-wise voltage is applied during gold electroplating. A lower voltage is applied initially to plate a thin and dense gold layer. Higher voltage is used later to increased the deposition rate and provide a less dense gold layer to reduce internal stress. Therefore, a thicker layer can be achieved. This is even more critical when one of the seed layer is a thin-film metal. High stress in electroplated layer will lift up the seed layer and cause delaminating and adhesion failure. The plating rates at different voltages are attached are listed in Table 1 below.

TABLE 1

Plating rates at different Voltages

| Voltage [volt] | Plating rate [µm/min] |
| --- | --- |
| −0.75 | 0.02 |
| −0.80 | 0.03 |
| −0.90 | 0.05 |
| −1.00 | 0.15 |
| −1.025 | 0.26 |

As plating conditions, including but not limited to the plating solution, surface area of the electrodes, pH, metal concentration, support electrolyte and the presence of additives, are changed the optimal control parameters will change according to basic electroplating principles.

SEM micrographs record the surface appearance before plating. The surface is chemically and electrochemically cleaned before plating.

Figure 8B:
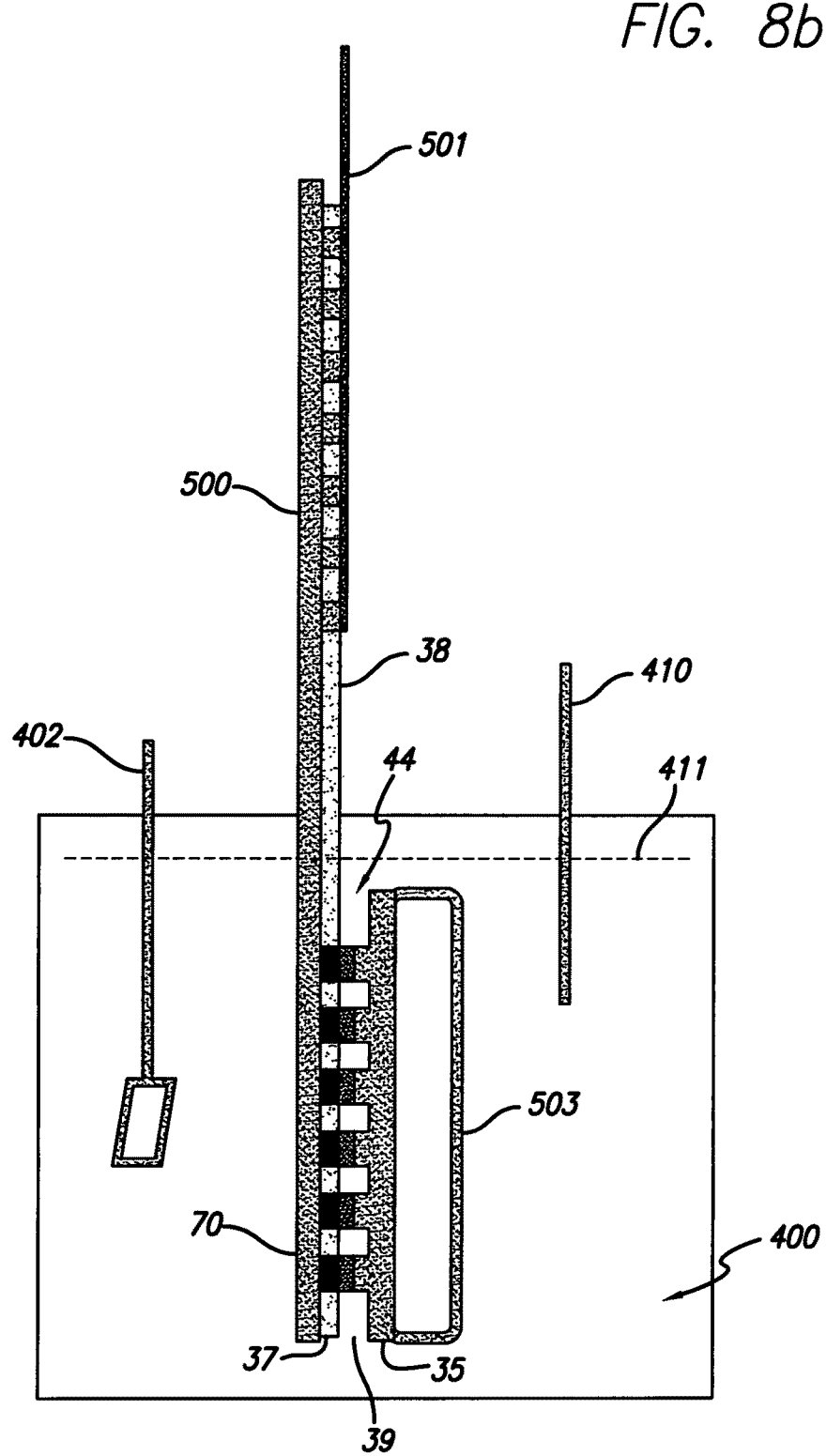
FIG. 8b is a cross sectional view of an electroplating cell for electroplated interconnecting.

The electrodes in the test cell 400 are arranged, so that the bonding assembly 70 (cathode) is physically parallel with the common electrode 402 (anode). The reference electrode 410 is positioned beside the bonding assembly 70. The plating solution is added to electroplating solution level 411. The solution is comprised of about 80 millimoles ammonium gold sulfite in about 400 millimoles phosphate buffer solution. The amount of solution used depends on the number of interconnection bonding 39 to be plated. The means for mixing 414, preferably a magnetic stirrer, is activated as shown in FIGS. 7 and 8b.

To use the thin-layer cell electroplating technique plating Pt or other metals connects the vias to a thin film electrode array (TFEA) pads. This technique will result in a direct connecting of Pt vias to Pt pads on TFEA without using conductive Pt epoxy. A schematic diagram of electroplating cell is shown in FIG. 8a. The assembly is carried out in three steps.

(1) Building up the height of Pt pads on TFEA and the height of vias on the ceramic (optional);

(2) Aligning the TFEA pads with the vias and keeping the TFEA in parallel with the ceramic and keeping the gap very small by using a spacer to control the gap if necessary;

(3) Immersing the assembly in plating solution and plating Pt or other metals to connect the pads with vias.

Electrode arrays on TFEA are covered with Cu or other active metals through electroplating or through thin-film process. Cu can be removed by electrochemical and/or chemical process after this process or after all production is completed.

The Cu layer also protects the Pt electrode surface from fouling by silicone or other contaminates. Vias with on Ceramic are patterned with Cu or other active metals through the thick-film or thin-film processes.

FIG. 8b shows a schematic view of an electroplating cell 400 for interconnecting. The Pt electroplating can be controlled by current or potential. An external potentiostat and/or chip 503 can be used for controlling the electroplating processes. Depending on electrical connection methods, either TFEA pads 37 or vias will be served as the cathode during the electroplating. TFEA pads 37 and vias can also be alternated as the cathode or both served as the cathode. Electroplating can be under dc or ac (square-wave) control. A reference electrode 410 is used for potential control and measurements. A Pt common electrode 402 is used as the anode during Pt electro-deposition. Cu layer 501 is applied short-circuiting all electrodes. Glass or ceramic support 500 is provided for TFEA 38. Substrate 44 is ceramic and contains Pt contacts 35 and is the bottom of the Nb Can with chip 503. Bonding assembly 70 contains electroplated Pt 39 connecting pads Pt 37 on TFEA 38 and Pt contacts 35 on ceramic 44.

A constant voltage is generated by a potentiostat 406 in the constant voltage plating. In the case of pulse voltage plating, the voltage waveform is generated, preferably with a 1 msec pulse width as a 500 Hz square wave. While for the pulse current plating, the pulse voltage waveform is converted to a current signal through a voltage to current converter 406.

In the case of pulse current, the response electrode voltage versus Ag/AgCl reference electrode is monitored using an oscilloscope (Tektronix TDS220 Oscilloscope). The current amplitude is adjusted so that the cathodic peak voltage reaches about −1.0 volts versus the Ag/AgCl reference electrode 410. During plating, the electrode voltage tends to decrease with plating time. The current amplitude is frequently adjusted so that the electrode voltage is kept within −0.9 to −1.1 v range versus Ag/AgCl reference electrode 410. When the specified plating time is reached, the current is eliminated. The cathode is rinsed in deionized water thoroughly. Typical plating time is in the range of about 5 to 120 minutes, preferably 20 to 80 minutes.

Figure 11:
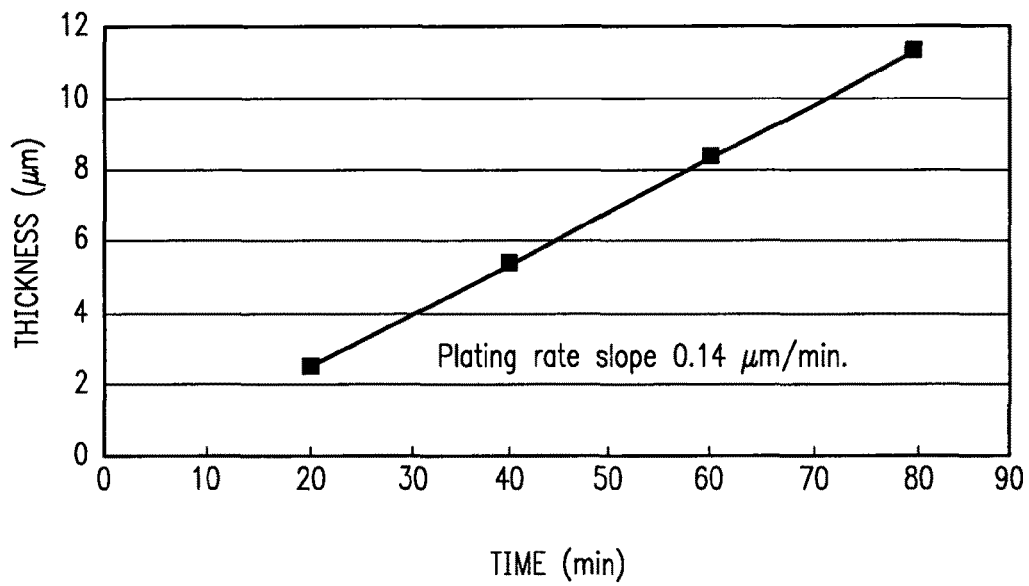
FIG. 11 is a thickness v. time plot of showing gold electrodeposition rate is constant.

The plated surface is examined under an optical microscope. Optical photomicrographs are taken at both low and high magnifications to record the image of the surface. The plated samples are profiled with a surface profilometer to measure the dimensions of the plated pads or bindings. The total plated pads or bonding has a total height of about 5 to 20 um and a diameter of 5 to 500 um. The deposition rate is a constant at a given voltage (see FIG. 11). The deposition rate is determined on the gold electroplating of 20 um openings under a constant voltage of −1.025 volts vs. a Ag/AgCl reference electrode.

After plating, the response current or pulsing current amplitudes are averaged for the total plating time and recorded. It has been demonstrated that the current density increases exponentially with increase in cathode electroplating voltages (See FIG. 10). The smaller the sample holes, the higher the current density required (see FIG. 9).

Figure 12:
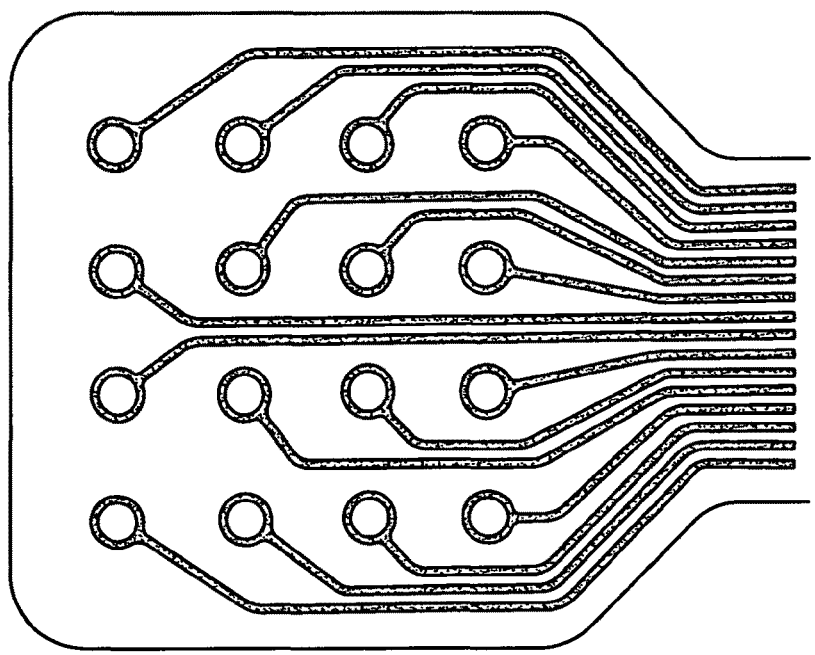
FIG. 12 is an optical image of gold electroplated polyimide surface.
Figure 13A:
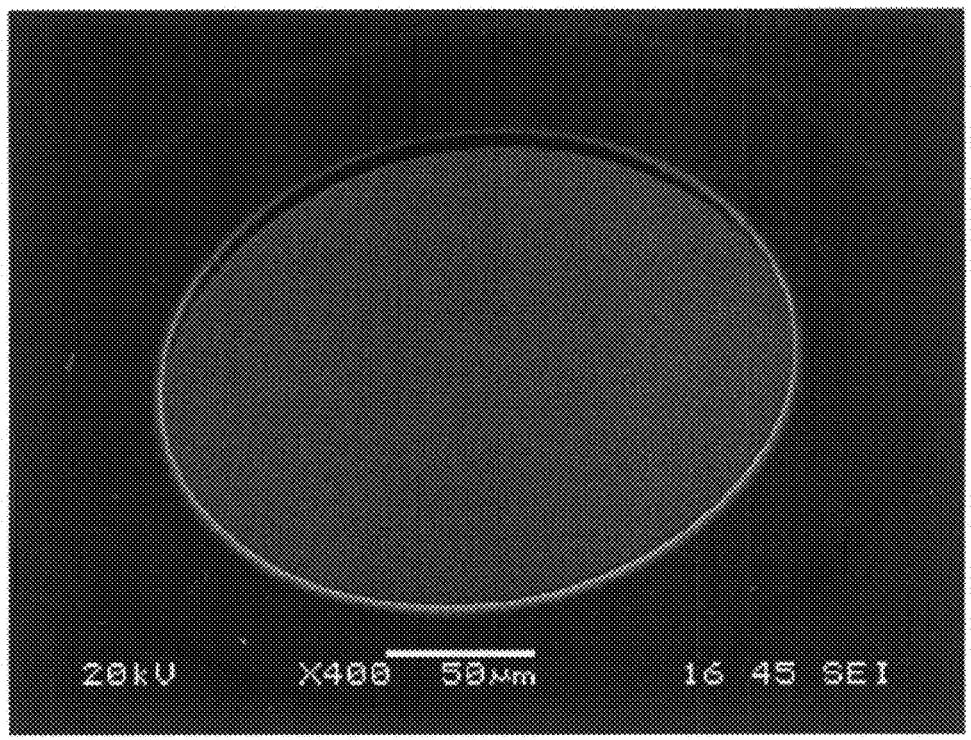
FIG. 13a is a scanning electron micrograph of a polyimide surface before plating magnified 400 times.
Figure 13B:
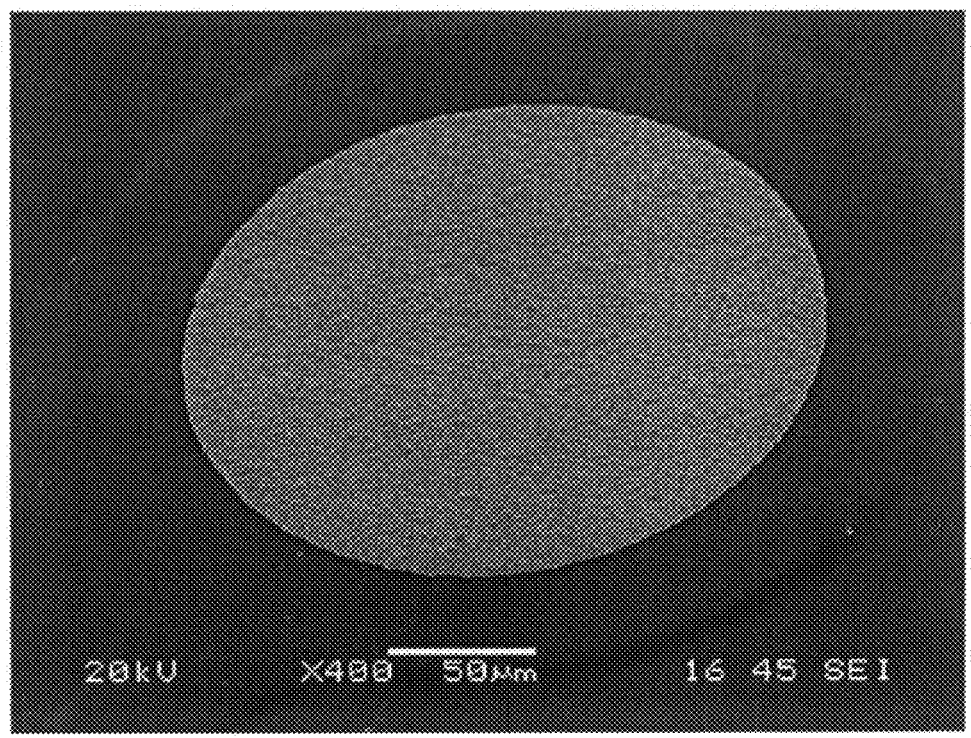
FIG. 13b is a scanning electron micrograph of electrochemically deposited interconnection pads magnified 400 times.

An illustrative example of a plated gold contact pads to the present invention are micrographs produced on a Nikon optical microscope (see FIG. 12) and a Scanning Electron Microscope (SEM) at 850× taken by a JEOL JSM5910 microscope, FIGS. 13a and 13b.

The following example is illustrative of electroplating platinum as a contact pads and interconnection binding 37, according to the present invention.

EXAMPLE

A flexible electrically insulating substrate comprised of a first substrate 38 and a second substrate 40 of polyimide having a total thickness of 6 µm. It had 16 first substrate holes 39 (FIG. 6b). The pads 37 with 200 µm openings on flex substrate 38 were made out of platinum.

The assembly was cleaned by rinsing three times in 10% HCl. It was further prepared by bubbling for 30 seconds at −3.5 V and +4 V for 3 cycles in 0.5 M sulphuric acid. Finally, it was rinsed in deionized water.

The electroplating set up according to FIGS. 6, 7 and 8b was comprised of an electroplating cell 400 that was a 100 ml beaker with an electroplating solution level 411 at about the 75 ml level. The solution was comprised of about 80 millimoles ammonium gold sulfite in about 400 millimoles phosphate buffer solution.

The means for mixing 414 was a magnetic stirrer, which was activated. The constant voltage of −0.75 V to −1.025 V with different step time versus Ag/AgCl reference electrode 410 were generated by an EG&G M273 potentiostat. The current is recorded and the current density and charge density were calculated. The response current amplitude was increased within the initial 20 seconds generating a current peak, and then reducing to a long flat current. The electroplating steps and response current densities and charge densities are listed in Table 2 below.

TABLE 2

Parameters of Gold Electroplating on Platinum for Interconnection Bonding

| Voltage Step | Voltage [Volts] | Time [minutes] | Average Charge [mC] | Average current density [mA/cm²] |
|---|---|---|---|---|
| 1 | −0.75  | 30 | −1.66  | 0.20 |
| 2 | −0.80  | 20 | −1.49  | 0.26 |
| 3 | −0.85  | 10 | −0.84  | 0.30 |
| 4 | −0.90  | 10 | −1.33  | 0.47 |
| 5 | −0.95  | 10 | −1.96  | 0.69 |
| 6 | −0.975 | 10 | −2.65  | 0.94 |
| 7 | −1.00  | 10 | −3.58  | 1.27 |
| 8 | −1.025 | 50 | −29.0  | 2.05 |

The average current density was 660 mA/cm², which generated response voltages of −0.5 to −0.7 volts, where the voltage was controlled by the current. A 1 msec pulse width square wave was generated by an HP 33120A Arbitrary Waveform Generator. The pulse was converted to a current signal through a voltage to current converter 406. The pulse current was typically about 1 msec in pulse width as a 500 Hz square wave. The resulting plated gold bonding 39 was about 20 um high tall, with about 15 um of the height extending above the polyimide substrate. The plated platinum gold bonding was strong, and electrically conductive. A pull test on the adhesion of the plated gold layer was carried out. A gold wire is resistively welded on the plated gold surface. All pull tests resulted in the failure of the gold wire to gold surface which indicates that the adhesion of plated gold to the seed layer is good.

Scanning Electron Microscope (SEM)/energy dispersive analysis (EDAX™) analysis were performed on the electroplated substrate 38. SEM micrographs of the plated surface were taken showing its as-plated surface, FIG. 13b. Energy dispersed analysis demonstrated that the plated 38 was pure gold, with no detectable oxygen.

Accordingly, what has been shown is an improved flexible circuit with an electronics control unit attached thereto, which is suitable for implantation in living tissue and to transmit electrical impulses to the living tissue. Obviously, many modifications and variations of the present invention are possible in light of the above teachings. It is therefore to be understood that, within the scope of the appended claims, the invention may be practiced other than as specifically described.

What we claim is:

1. An electronics device comprising:
   a substrate containing at least one contact;
   a flexible assembly containing at least one bond pad defining an opening;
   an electroplated bonding between said at least one contact and said at least one bond pad and through said opening that forms a rivet shaped bond between said substrate and said flexible assembly together;
   said electroplated bonding comprised of biocompatible material comprising platinum or gold; and
   said biocompatible material having a first dense layer of platinum or gold said contact and a second less dense layer of platinum or gold to reduce internal stresses and increase the strength of the rivet shaped bond on said first dense layer;
   wherein the first dense layer and the second less dense layer consist of the same elemental composition.

2. The device according to claim 1 wherein said device is implantable.

3. The device according to claim 1 wherein said contact is a routing.

4. The device according to claim 1 wherein said electroplated bonding comprises platinum alloy or platinum-iridium.

5. The device according to claim 4 wherein electroplated bonding is accomplished at a current density of 0.5 to 40 mA/cm$^2$.

6. The device according to claim 1 wherein said flexible assembly comprises polyimide.

7. The device according to claim 1 wherein said substrate comprises a biocompatible ceramic bonded to an integrated circuit with a hermetic coating.

8. The device according to claim 7 wherein said biocompatible ceramic comprises alumina.

9. The device according to claim 1 wherein:
   at least a part of said substrate forms an electronics package; and
   said electronics package encapsulates electronics.

10. The device according to claim 1 wherein said substrate is an electrically insulated integrated circuit.

11. The device according to claim 1 wherein said flexible assembly is a thin integrated circuit with a hermetic coating.

12. The device according to claim 1 wherein:
   said biocompatible metal is comprised of gold or platinum; and
   said biocompatible gold or platinum having a first dense layer that is formed with a plating voltage and a second less dense layer that is formed at a higher plating voltage with increased deposition rate.

* * * * *